United States Patent
Przewosny

(10) Patent No.: US 7,145,011 B2
(45) Date of Patent: Dec. 5, 2006

(54) METHOD FOR THE PRODUCTION OF SUBSTITUTED 1,2,3,4-TETRAHYDROQUINOLINE-2-CARBOXYLIC ACIDS

(75) Inventor: Michael Thomas Przewosny, Aachen (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 10/896,728

(22) Filed: Jul. 22, 2004

(65) Prior Publication Data

US 2005/0004366 A1 Jan. 6, 2005

Related U.S. Application Data

(63) Continuation of application No. PCT/EP03/00082, filed on Jan. 8, 2003.

(51) Int. Cl.
*C07D 221/06* (2006.01)
*C07D 221/12* (2006.01)

(52) U.S. Cl. .................. 546/108; 546/93; 546/110; 546/165

(58) Field of Classification Search .................. 546/93, 546/108, 110, 165
See application file for complete search history.

(56) References Cited

U.S. PATENT DOCUMENTS 6,699,877 B1 *   3/2004   Gerlach et al. ............. 514/291

FOREIGN PATENT DOCUMENTS

WO         WO 01/58875 A2       8/2001

OTHER PUBLICATIONS

Rieke et al., "Magnesium Activation", Handbook of Grignard Reagents, 1996, pp. 53-77.

* cited by examiner

*Primary Examiner*—D. Margaret Seaman
(74) *Attorney, Agent, or Firm*—Perman & Green, LLP

(57) ABSTRACT

The invention relates to a method for the production of substituted 1,2,3,4-tetrahydroquinoline-2-carboxylic acids, i.e. 7,9-dichlor-3a,4,5,9b-tetrahydro-3H-cyclopental[c]quinoline-4-carboxylic acid.

10 Claims, No Drawings

METHOD FOR THE PRODUCTION OF SUBSTITUTED 1,2,3,4-TETRAHYDROQUINOLINE-2-CARBOXYLIC ACIDS

This application is a continuation of international application number PCT/EP03/00082 filed Jan. 8, 2003, status pending, and which claims priority to German Patent Application DE 102 02 864.8 filed Jan. 24, 2002.

The present invention relates to a process for the production of substituted 1,2,3,4-tetrahydroquinoline-2-carboxylic acids, such as 7,9-dichloro-3a,4,5,9b-tetrahydro-3H-cyclopenta[c]quinoline-4-carboxylic acid.

Substituted 1,2,3,4-tetrahydroquinoline-2-carboxylic acids, such as 7,9-dichloro-3a,4,5,9b-tetrahydro-3H-cyclopenta[c]quinoline-4-carboxylic acid of the formula A below are NMDA antagonists, which bind selectively to the glycineB binding site of the NMDA ion channel. The compounds are analgesically active and are suitable for the treatment of pain, in particular of chronic or neuropathic pain (WO 01/58875).

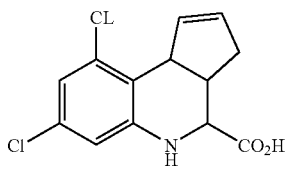

According to the teaching of WO 01/58875, substituted 1,2,3,4-tetrahydroquinoline-2-carboxylic acids are obtained by the Grieco three-component synthesis. In this imino Diels-Alder reaction, aromatic amines, glyoxylic acid alkyl esters and olefins are reacted with acid catalysis by trifluoroacetic acid to yield substituted 1,2,3,4-tetrahydoquinoline-2-carboxylic acid esters, from which the carboxylic acids must be obtained by saponification.

Disadvantages of this known process are the use of trifluoroacetic acid, the two-stage method and the relatively long reaction time of up to 24 hours.

The object of the present invention was accordingly to provide a process for the production of substituted 1,2,3,4-tetrahydroquinoline-2-carboxylic acids, such as 7,9-dichloro-3a,4,5,9b-tetrahydro-3H-cyclopenta[c]quinoline-4-carboxylic acid, which is distinguished by a single-stage method, short reaction times, i.e. of less than one hour, and an elevated yield.

This object has been achieved by the single-stage process according to the invention hereinafter disclosed for the production of substituted 1,2,3,4-tetrahydroquinoline-2-carboxylic acids, such as 7,9-dichloro-3a,4,5,9b-tetrahydro-3H-cyclopenta[c]quinoline-4-carboxylic acid.

The present invention accordingly provides a process for the production of a substituted 1,2,3,4-tetrahydroquinoline-2-carboxylic acid of the general formula I,

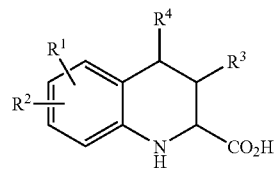

in which $R^1$ and $R^2$, identical or different, denote hydrogen, a halogen, a trifluoromethyl group, a linear or branched, saturated or unsaturated aliphatic $C_{1-6}$ residue optionally attached via oxygen or together form a $C_{3-5}$ chain with formation of a fused ring, $R^3$ and $R^4$ together form a saturated or unsaturated aliphatic $C_{3-5}$ chain with formation of a cycloaliphatic ring or $R^3$ denotes a linear or branched, saturated or unsaturated aliphatic $C_{1-6}$ residue, a cycloaliphatic $C_{3-6}$ residue, an aryl residue or a heteroaryl residue, wherein the aryl or heteroaryl residue may optionally be substituted with halogen, a linear or branched, saturated or unsaturated $C_{1-6}$ alkyl residue and/or a linear or branched, saturated or unsaturated $C_{1-6}$ alkoxy residue, and $R^4$ denotes a linear or branched, saturated or unsaturated aliphatic $C_{1-6}$ residue, an aryl or heteroaryl residue, wherein the above-stated residues may optionally be attached via a heteroatom and/of the aryl or heteroaryl residue may be substituted with halogen, a linear or branched, saturated or unsaturated $C_{1-6}$ alkyl residue, an aryl residue, a heteroaryl residue, a cyano group, an aldehyde group, a residue of the formula $-C_nF_{2n+1}$, in which n denotes an integer from 1–6, and/or a residue of the formula $-C(OR^5)_2$, $-C(O)-NR^5_2$ or $-YR^5$ and/or the aryl or heteroaryl residue not attached via a heteroatom may optionally be part of a polycyclic system, wherein $R^5$ denotes a linear or branched, saturated or unsaturated aliphatic $C_{1-6}$ residue, an aryl or heteroaryl residue and Y denotes a heteroatom or a bridge of the formula $-C(O)-O-$ or $-C(O)-S$, by simultaneously reacting an optionally substituted aniline of the formula II, in which $R^1$ and $R^2$ have the above-stated meaning,

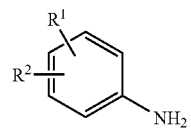

glyoxylic acid or glyoxylic acid hydrate and
an olefin of the formula III, in which $R^3$ and $R^4$ have the above-stated meaning,

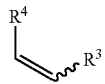

in a suitable solvent with microwave irradiation, preferably throughout the entire reaction time, wherein the olefin of the formula III and the glyoxylic acid or glyoxylic acid hydrate are introduced in excess.

A preferred process is one in which
a compound of the formula II is used as the optionally substituted aniline,
in which
$R^1$ and $R^2$, identical or different, denote hydrogen, chlorine, a methyl group, a methoxy group or a trifluoromethyl group, and
a compound of the formula III is used as the olefin, in which
$R^3$ and $R^4$ together form a saturated or unsaturated aliphatic $C_{3-4}$ chain with formation of a cycloaliphatic ring or
$R^3$ denotes a linear or branched, saturated or unsaturated aliphatic $C_{1-3}$ residue, a cycloaliphatic $C_{5-6}$ residue, an aryl residue or a heteroaryl residue, wherein the aryl or heteroaryl residue may optionally be substituted with a linear or branched, saturated or unsaturated $C_{1-3}$ alkoxy residue, and
$R^4$ denotes a linear or branched, saturated or unsaturated aliphatic $C_{1-3}$ residue, an aryl or heteroaryl residue, wherein the above-stated residues may optionally be attached via oxygen or sulfur and/or the aryl or heteroaryl residue may be substituted with halogen, a linear or branched, saturated or unsaturated $C_{1-3}$ alkyl residue, an aryl residue, a heteroaryl residue, a cyano group, an aldehyde group, a residue of the formula —$C_nF_{2n+1}$, in which n denotes an integer from 1–3, and/or a residue of the formula —$C(OR^5)_2$, —$C(O)$—$NR^5_2$ or —$YR^5$ and/or the aryl or heteroaryl residue not attached via oxygen or sulfur may optionally be part of a polycyclic system, wherein
$R^5$ denotes a linear or branched, saturated or unsaturated aliphatic $C_{1-3}$ residue, an aryl or heteroaryl residue and
Y denotes oxygen, sulfur or a bridge of the formula —$C(O)$—$O$— or —$C(O)$—$S$.

A particularly preferred process is one in which a compound of the formula II is used as the optionally substituted aniline,
in which
$R^1$ and $R^2$ denote hydrogen and chlorine or a methyl group in position 6 or 7, in each case chlorine or a methyl group in position 6 and 7 or in position 5 and 7, and
a compound of the formula III is used as the olefin, in which
$R^3$ and $R^4$ together form a saturated or unsaturated aliphatic $C_{3-4}$ chain with formation of a cycloaliphatic ring or
$R^3$ denotes a phenyl residue optionally substituted with an alkoxy group, preferably a methoxy group, and
$R^4$ denotes a methyl group, a methoxy group or a phenyl residue optionally substituted with halogen and/or a methyl group.

The process according to the invention is very particularly preferably used for the production of 7,9-dichloro-3a,4,5,9b-tetrahydro-3H-cyclopenta[c]quinoline-4-carboxylic acid of the formula A by reaction of 3,5-dichloroaniline, glyoxylic acid or glyoxylic acid hydrate and cyclopentadiene.

The optionally substituted aniline of the formula II, the glyoxylic acid or the glyoxylic acid hydrate and the olefin of the formula III are preferably reacted in a molar ratio of 1:1.5–3:1.5–3.

Acetonitrile is preferably used as the solvent. The solvent is used in a quantity sufficient to dissolve the starting compounds at 25° C.

The reaction is preferably performed at a temperature of 40–80° C., particularly preferably at 50–60° C. The reaction preferably proceeds isothermally.

The reaction according to the invention proceeds in less than one hour, preferably in less than 30 minutes, particularly preferably in 5–15 minutes.

Microwave irradiation is performed using an apparatus with a power of 100–1200 watts, preferably of 600–1000 watts. Microwave irradiation preferably proceeds throughout the entire reaction time.

The reaction may be performed discontinuously or continuously, preferably discontinuously. The reaction is preferably performed in a closed, pressure-resistant, inert vessel. In a production process, it is possible to use continuous flow reactors or microreactor technology.

The compound of the general formula I is preferably isolated by removing the solvent or filtering out the sparingly soluble compound of the general formula I. In so doing, a compound of the general formula I is conventionally obtained which is already of analytical purity.

If necessary, the isolated compound of the general formula I may be purified by washing it preferably with a suitable solvent, particularly preferably with a nonpolar organic solvent, very particularly preferably hexane or acetonitrile and/or by recrystallising the compound.

The compound of the formula I may also be converted into the salts or solvates thereof. The corresponding salt may be formed by addition of a base, such as sodium hydroxide, or the corresponding hydrochloride by addition of hydrochloric acid.

The starting compounds for the synthesis are commercially obtainable or may be obtained by simple reactions known to the person skilled in the art.

Advantages of the production process according to the invention for 1,2,3,4-tetrahydroquinoline-2-carboxylic acids are the single-stage method, the extraordinarily short reaction times and the elevated purity of the products obtained, which means that it is possible to dispense with elaborate purification processes, such as for example chromatography.

Substituted 1,2,3,4-tetrahydroquinoline-2-carboxylic acids of the general formula I, such as 7,9-dichloro-3a,4,5,9b-tetrahydro-3H-cyclopenta[c]quinoline-4-carboxylic acid, are used as pharmaceutical preparations, preferably for the treatment of pain, in particular of chronic or neuropathic pain.

EXAMPLES

Description of the Syntheses

The chemicals and solvents used were purchased from conventional suppliers (Acros, Fluka, Merck).

The reactions with microwave irradiation were performed in a laboratory microwave oven, model MLS ETHOS 600 from MLS-GmbH (D-88299 Leutkirch, Auenweg 37, Germany).

Thin-layer chromatography was performed on RP-8 TLC plates with a fluorescence indicator (Merck, Darmstadt) using the following mobile solvent mixture: methanol/water/NaCl 12:5:3. Detection was performed by staining in an iodine chamber.

$^1$H-NMR spectra were measured with a spectrometer (Avance DPX 300 MHz) from Bruker Analytik GmbH, Silberstreifen 4, D-76287 Rheinstetten.

ESI-MS spectra were measured with an instrument (model Finnigan LCQ) from Thermoquest, Analytische Systeme GmbH, Boschring 12, D-63329 Egelsbach.

GC analysis was performed on an HP 6890 gas chromatograph with (PTV injector) and a 5973 Mass Selective Detector made by Hewlett Packard coupled thereto.

Comparative Example

Known two-stage synthesis of 7,9-dichloro-3a,4,5,9b-tetrahydro-3H-cyclopenta[c]quinoline-4-carboxylic acid a) Synthesis of 7,9-dichloro-3a,4,5,9b-tetrahydro-3H-cyclopenta[c]quinoline-4-carboxylic acid ethyl ester 1.62 g of 3,5-dichloroaniline (10 mmol) and 1.84 ml of glyoxylic acid ethyl ester (10 mmol) (50% in toluene) were dissolved in 20 ml of acetonitrile. 0.77 ml of trifluoroacetic acid (10 mmol) and 1.40 g of cyclopentadiene (30 mmol) (freshly distilled) were added and stirred overnight at 40° C. Saturated sodium hydrogencarbonate solution was then added, the phases separated, the aqueous phase extracted three times with diethyl ether and the organic phase washed to neutrality with water, dried over magnesium sulfate and evaporated. The colourless residue was further reacted without purification.

GC/MS ($C_{15}H_{15}Cl_2NO_2$) Calculated: 312.20. found: 311 ($M^+$), 238 ($M^+$—$CO_2CH_2CH_3$). $^1$H-NMR spectrum ($d_6$-DMSO/TMS$_{ext.}$): δ=1.25 ppm (t, 3H, $CH_3$); 2.20–2.35 ppm (m, 2H, $CH_2$); 3.15 ppm (m, 1H, CH); 4.00 ppm (m, 1H, CH); 4.05–4.20 ppm (m, 3H, $CH_2O$ and CH; 5.65 ppm (m, 1H, CH); 5.85 ppm (m, 1H, CH); 6.10 ppm (s, 1H, aryl-H), 6.90 ppm (s, 1H, aryl-H).

b) Synthesis von 7,9-dichloro-3a,4,5,9b-tetrahydro-3H-cyclopenta[c]quinoline-4-carboxylic acid 7,9-Dichloro-3a,4,5,9b-tetrahydro-3H-cyclopenta[c]quinoline-4-carboxylic acid ethyl ester, which has been obtained according to reaction a), (10 mmol) was dissolved in 10 ethanol and with combined with 1 ml of 6N sodium hydroxide solution and stirred overnight. The mixture was then evaporated to dryness, the residue combined with 10 ml of water and the aqueous phase extracted three times with diethyl ether. The aqueous phase was adjusted to pH 1 with 1M hydrochloric acid and extracted five times with dichloromethane. The combined organic phase was washed with water, dried over magnesium sulfate and evaporated. A colourless mass of crystals was obtained. The yield of the crude product was 96% of theoretical.

ESI-MS ($C_{13}H_{11}Cl_2NO_2$) Calculated: 284.14. found (positive mode): 284.1. ($MH^+$), 238.4 ($MH^+$—$CO_2$), 218.1 ($MH^+$—$C_5H_5$). $^1$H-NMR ($d_4$-methanolTMS$_{int.}$): δ=2.30–2.60 ppm (m, 2H, $CH_2$); 3.40 ppm (m, 1H, CH); 4.00 ppm (d, 1H, CH); 4.25 ppm (d, 1H, CH); 5.70 ppm (m, 1H, olefin-H); 5.90 ppm (s, 1H, olefin-H); 6.70 ppm (s, 2H, 2×aryl-H).

Example

Synthesis of 7,9-dichloro-3a,4,5,9b-tetrahydro-3H-cyclopenta[c]quinoline-4-carboxylic acid 1.14 g of 3,5-dichloroaniline (10 mmol), 0.97 g of glyoxylic acid hydrate (15 mmol) and 1.40 g of cyclopentadiene (freshly distilled) (30 mmol) were dissolved in 20 ml of acetonitrile in a closable Teflon vessel and heated to 50° C. within one minute in a microwave oven with a power of 800 watts and kept at this temperature for five minutes with further microwave irradiation. The vessel was then placed in ice water, cautiously opened and evaporated in a rotary evaporator. The mass of crystals obtained was washed with hexane and dried. A colourless mass of crystals was obtained in a quantity of 1.95 g (98% of theoretical).

ESI-MS ($C_{13}H_{11}Cl_2NO_2$) Calculated: 284.14. found (negative mode): 282.3 (M-H), 238.3 (M—$CO_2$); (positive mode): 286.0 ($MH^+$), 240.2 (M—$CO_2$). $^1$H-NMR ($d_6$-DMSO/TMS$_{ext.}$) δ=2.20–2.40 ppm (m, 2H, $CH_2$); 3.30 ppm (m, 1H, CH); 3.90 ppm (m, 1H, CH); 4.15 ppm (m, 1H, CH); 5.70 ppm (m, 1H, olefin-H); 5.90 ppm (m, 1H, olefin-H); 6.05 ppm (s, 1H, NH); 7.75 ppm (s, 1H, aryl-H); 7.95 ppm (s, 1H, aryl-H); 13.0 ppm (s, 1H, $CO_2H$).

The invention claimed is:

1. A process for the production of a substituted 1,2,3,4-tetrahydroquinoline-2-carboxylic acid of the general formula I,

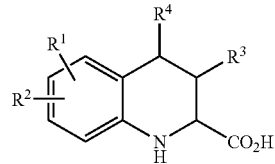

in which $R^1$ and $R^2$, identical or different, denote hydrogen, a halogen, a trifluoromethyl group, a linear or branched, saturated or unsaturated aliphatic $C_{1-6}$ residue optionally attached via oxygen or together form a $C_{3-5}$ chain with formation of a fused ring, $R^3$ and $R^4$ together form a saturated or unsaturated aliphatic $C_{3-5}$ chain with formation of a cycloaliphatic ring or $R^3$ denotes a linear or branched, saturated or unsaturated aliphatic $C_{1-6}$ residue, a cycloaliphatic $C_{3-6}$ residue, an aryl residue or a heteroaryl residue, wherein the aryl or heteroaryl residue may optionally be substituted with halogen, a linear or branched, saturated or unsaturated $C_{1-6}$ alkyl residue and/or a linear or branched, saturated or unsaturated $C_{1-6}$ alkoxy residue, and $R^4$ denotes a linear or branched, saturated or unsaturated aliphatic $C_{1-6}$ residue, an aryl or heteroaryl residue, wherein the above-stated residues may optionally be attached via a heteroatom and/or the aryl or heteroaryl residue may be substituted with halogen, a linear or branched, saturated or unsaturated $C_{1-6}$ alkyl residue, an aryl residue, a heteroaryl residue, a cyano group, an aldehyde group, a residue of the formula —$C_nF_{2n+1}$, in which n denotes an integer from 1–6, and/or a residue of the formula $C(OR^5)_2$, —C(O)—$NR^5_2$ or —$YR^5$ and/or the aryl or heteroaryl residue not attached via a heteroatom may optionally be part of a polycyclic system, wherein $R^5$ denotes a linear or branched, saturated or saturated aliphatic $C_{1-6}$ residue, an aryl or heteroaryl residue and Y denotes a heteroatom or a bridge of the formula —C(O)—O— or —C(O)—S, by simultaneously reacting an optionally substituted aniline of the formula II, in which $R^1$ and $R^2$ have the above-stated meaning,

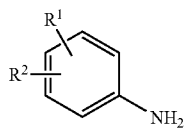

glyoxylic acid or glyoxylic acid hydrate and
an olefin of the formula III, in which $R^3$ and $R^4$ have the above-stated meaning,

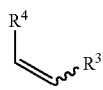

in a suitable solvent with microwave irradiation, preferably throughout the entire reaction time, wherein the olefin of the formula III and the glyoxylic acid or glyoxylic acid hydrate are introduced in excess.

2. A process according to claim 1, characterised in that a compound of the formula II, in which $R^1$ and $R^2$, identical or different, denote hydrogen, chlorine, a methyl group, a methoxy group or a trifluoromethyl group, is used as the optionally substituted aniline and
a compound of the formula III is used as the olefin, in which
$R^3$ and $R^4$ together form a saturated or unsaturated aliphatic $C_{3-4}$ chain with formation of a cycloaliphatic ring or
$R^3$ denotes a linear or branched, saturated or unsaturated aliphatic $C_{1-3}$ residue, a cycloaliphatic $C_{5-6}$ residue, an aryl residue or a heteroaryl residue, wherein the aryl or heteroaryl residue may optionally be substituted with a linear or branched, saturated or unsaturated $C_{1-3}$ alkoxy residue, and
$R^4$ denotes a linear or branched, saturated or unsaturated aliphatic $C_{1-3}$ residue, an aryl or heteroaryl residue, wherein the above-stated residues may optionally be attached via oxygen or sulfur and/or the aryl or heteroaryl residue may be substituted with halogen, a linear or branched, saturated or unsaturated $C_{1-3}$ alkyl residue, an aryl residue, a heteroaryl residue, a cyano group, an aldehyde group, a residue of the formula —$C_nF_{2n+1}$, in which n denotes
an integer from 1–3, and/or a residue of the formula —$C(OR^5)_2$, —$C(O)$—$NR^5_2$ or —$YR^5$ and/or the aryl or heteroaryl residue not attached via oxygen or sulfur may optionally be part of a polycyclic system, wherein $R^5$ denotes a linear or branched, saturated or unsaturated aliphatic $C_{1-3}$ residue, an aryl or heteroaryl residue and
Y denotes oxygen, sulfur or a bridge of the formula —C(O)—O— or —C(O)—S.

3. A process according to claim 1, characterised in that a compound of the formula II, in which $R^1$ and $R^2$ denote hydrogen and chlorine or a methyl group in position 6 or 7, in each case chlorine or a methyl group in position 6 and 7 or in position 5 and 7, is used as the optionally substituted aniline and a compound of the formula III is used as the olefin, in which
$R^3$ and $R^4$ together form a saturated or unsaturated aliphatic $C_{3-4}$ chain with formation of a cycloaliphatic ring or
$R^3$ denotes a phenyl residue optionally substituted with an alkoxy group, preferably a methoxy group, and
$R^4$ denotes a methyl group, a methoxy group or a phenyl residue optionally substituted with halogen or a methyl group.

4. A process according to claim 1, characterised in that the optionally substituted aniline of the formula II, the glyoxylic acid or the glyoxylic acid hydrate and the olefin of the formula III are reacted in a molar ratio of 1:1.5-3:1.5-3.

5. A process according to claim 1, characterised in that acetonitrile is used as the solvent.

6. A process according to claim 1, characterised in that the reaction is performed at 40–80° C., preferably at 50–60° C.

7. A process according to claim 1, characterised in that the compound of the general formula I is isolated by removing the solvent or filtering out the sparingly soluble compound of the general formula I.

8. A process according to claim 1, characterised in that the compound of the general formula I is purified by washing the isolated compound with a suitable solvent, preferably with a nonpolar organic solvent, particularly preferably hexane or acetonitrile, and/or recrystallising the compound.

9. A process according to claim 1, characterised in that a base, preferably sodium hydroxide, is added to the isolated and optionally purified compound of the general formula I to form the corresponding salt or hydrochloric acid is added to form the corresponding hydrochloride.

10. A process for the production of 7,9-dichloro-3a, 4,5, 9b-tetrahydro-3H-cyclopenta [c]quinoline-4-carboxylic acid according to claim 1, characterised in that 3,5-dichloroaniline, glyoxylic acid or glyoxylic acid hydrate and cyclopentadiene are reacted.

* * * * *